United States Patent
Milner et al.

(10) Patent No.: US 10,272,192 B2
(45) Date of Patent: Apr. 30, 2019

(54) SITE SPECIFIC DRUG DELIVERY DEVICE

(71) Applicant: Cook Medical Technologies LLC, Bloomington, IN (US)

(72) Inventors: Keith R. Milner, West Lafayette, IN (US); Triona Campbell, Jr., Killaloe (IE)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 814 days.

(21) Appl. No.: 14/621,501

(22) Filed: Feb. 13, 2015

(65) Prior Publication Data

US 2015/0231326 A1  Aug. 20, 2015

Related U.S. Application Data

(60) Provisional application No. 61/940,038, filed on Feb. 14, 2014.

(51) Int. Cl.
| | | |
|---|---|---|
| *A61M 5/14* | (2006.01) | |
| *A61M 25/00* | (2006.01) | |
| *A61M 25/04* | (2006.01) | |
| *A61F 9/00* | (2006.01) | |
| *A61F 2/14* | (2006.01) | |
| *A61F 2/01* | (2006.01) | |

(52) U.S. Cl.
CPC .............. *A61M 5/14* (2013.01); *A61F 2/15* (2015.04); *A61F 9/0008* (2013.01); *A61M 25/0074* (2013.01); *A61M 25/04* (2013.01); *A61F 2/01* (2013.01); *A61M 25/007* (2013.01); *A61M 2025/0057* (2013.01)

(58) Field of Classification Search
CPC ....... A61F 2/01; A61M 5/14; A61M 25/0074; A61M 2025/109; A61M 2025/1095; A61M 25/007; A61M 2025/0057; A61M 25/003; A61M 25/04; A61M 25/10
See application file for complete search history.

(56) References Cited

U.S. PATENT DOCUMENTS

| | | | |
|---|---|---|---|
| 5,181,911 A | 1/1993 | Shturman | |
| 5,336,178 A | 8/1994 | Kaplan et al. | |
| 5,405,334 A | 4/1995 | Roth et al. | |
| 5,599,306 A * | 2/1997 | Klein | A61M 25/104 604/103.01 |
| 5,713,863 A * | 2/1998 | Vigil | A61M 25/10 604/104 |
| 5,947,985 A | 9/1999 | Imram | |
| 6,074,339 A | 6/2000 | Gambale et al. | |
| 7,722,604 B2 | 5/2010 | Brown, III et al. | |

(Continued)

FOREIGN PATENT DOCUMENTS

WO   WO 2004/098697 A1   11/2004

*Primary Examiner* — Bradley J Osinski
*Assistant Examiner* — Nilay J Shah
(74) *Attorney, Agent, or Firm* — Brinks Gilson & Lione

(57) ABSTRACT

A drug delivery device is provided for directly treating a treatment site. The device allows body fluids to perfuse past the device while it is expanded to increase the amount of treatment time that is possible. The drug is delivered through a hollow helical tube that extends around a support structure. The hollow tube includes a series of lateral holes to allow the drug to directly reach the desired treatment site.

18 Claims, 3 Drawing Sheets

(56) References Cited

U.S. PATENT DOCUMENTS

| | | |
|---|---|---|
| 8,241,241 B2 | 8/2012 | Evans et al. |
| 8,257,340 B2 | 9/2012 | Saab |
| 8,382,908 B2 | 2/2013 | Vazales et al. |
| 2005/0021075 A1* | 1/2005 | Bonnette ................ A61F 2/013 606/200 |
| 2005/0113631 A1 | 5/2005 | Bolling et al. |
| 2007/0208367 A1* | 9/2007 | Fiorella ................ A61B 17/22 606/198 |
| 2010/0016831 A1 | 1/2010 | Bodenlenz et al. |
| 2010/0324472 A1 | 12/2010 | Wulfman |
| 2012/0101413 A1 | 4/2012 | Beetel et al. |
| 2012/0116351 A1* | 5/2012 | Chomas ................ A61F 2/013 604/508 |
| 2012/0259216 A1 | 10/2012 | Gerrans et al. |

* cited by examiner

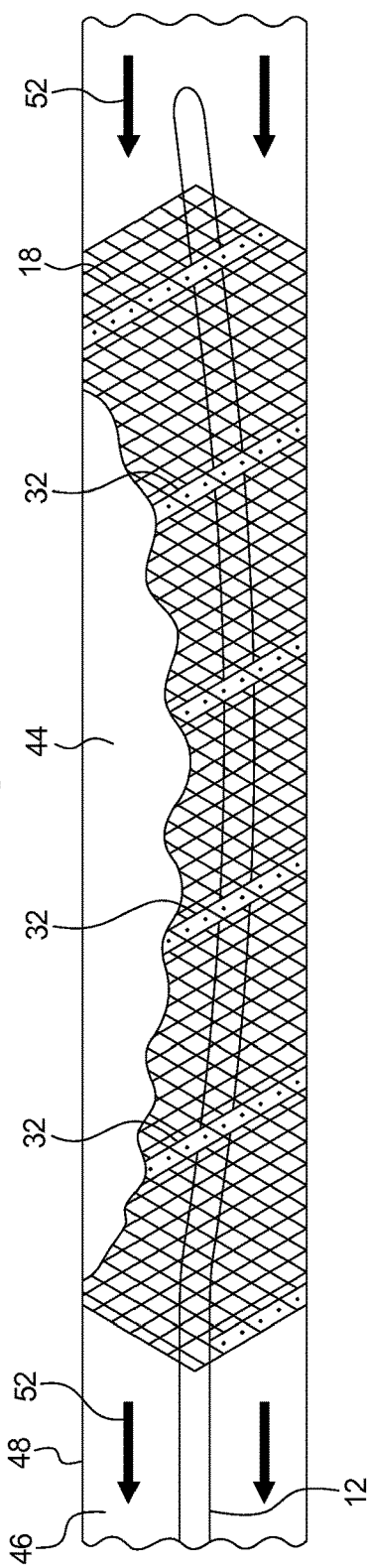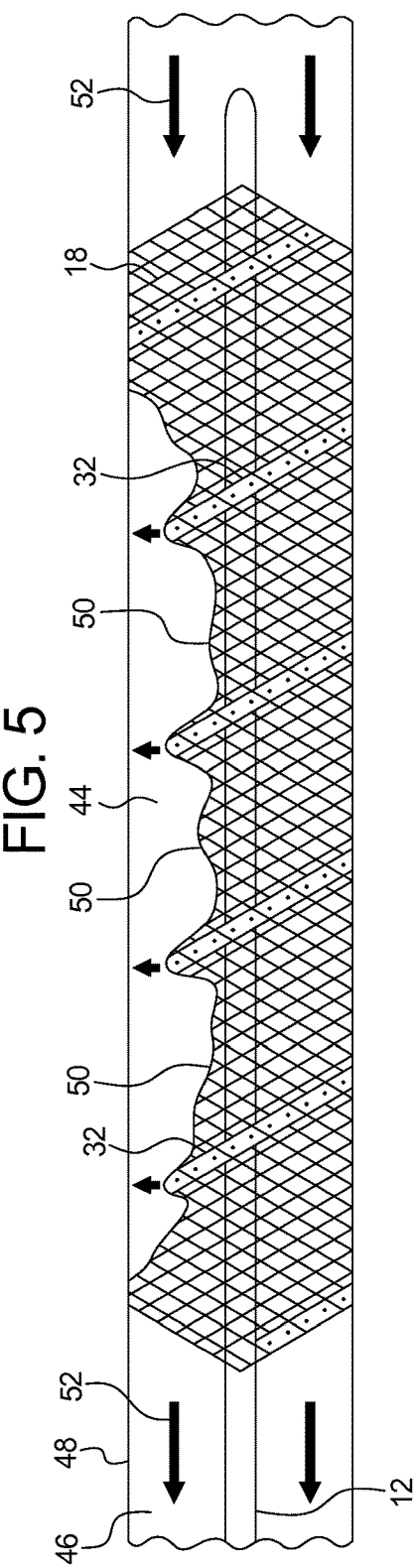

SITE SPECIFIC DRUG DELIVERY DEVICE

This application claims priority to U.S. Provisional Application No. 61/940,038, filed Feb. 14, 2014, which is hereby incorporated by reference herein.

BACKGROUND

The present invention relates generally to medical devices and more particularly to delivering a drug to a specific treatment site.

Various intraluminal procedures require the infusion of drugs to treat physiological conditions. For example, anti-restenosis drugs, such as paclitaxel, sirolimus or everolimus, are often used to treat atherosclerotic lesions when dilating the lesion to prevent tissue regrowth after intraluminal dilation procedures. This may be done, for example, with a balloon that is coated with the anti-restenosis drug. During the procedure the balloon may be inflated at the treatment site so that the outer surface of the balloon is pressed against the wall of the vessel. Since the outer surface of the balloon is coated with the anti-restenosis drug, the drug is pressed against the treatment site and is absorbed by the tissues of the vessel wall. While this approach has the advantage of applying the drug directly to the tissues where treatment is desired, it can be difficult to achieve the level of treatment desired since the balloon can only remain inflated for a short period of time. That is, conventional balloons fill the vessel lumen when inflated and block blood flow through the vessel. However, blood flow can typically be blocked for only a short period of time (e.g., usually less than 3 minutes) in order to prevent starving downstream tissues of blood and oxygen.

Another intraluminal drug delivery procedure involves the treatment of venous thrombi with drugs that dissolve or encourage dissolution of the thrombus, such as tissue plasminogen activator (tPA) or heparin. Typically, thrombolytic or anti-thrombotic drugs are administered with a catheter located near the desired treatment site. The drug is discharged from the distal end of the catheter and flows with the blood flow through the patient's vascular system. As the drug flows through the vessel, some of the drug is absorbed by the thrombus along the vessel wall. Unlike the balloon approach described above, this drug delivery approach can be administered over a longer period of time since the catheter does not block blood flow through the vessel and blood flow continues through the vessel during the procedure. However, a significant portion of the drug may not interact with the desired treatment site and may flow downstream away from the treatment site. This may have several disadvantages. For example, successful treatment of the thrombus may be prolonged since only some of the drug therapeutically treats the thrombus. Although this may lengthen the medical treatment, it is also possible that complete treatment of a thrombus may be difficult or impractical because of the limited therapeutic effect of such procedures. In addition, the significant portion of the drug that flows downstream can have other undesired effects. For example, other unknown thrombi in the vasculature may be loosened, which may cause undesirable side effects.

Accordingly, the inventors believe that an improved drug delivery device that applies a drug more directly to a treatment site while allowing blood flow through the vessel to permit longer treatments would be desirable.

SUMMARY

A drug delivery device is described with a support structure and a plurality of openings to allow fluid flow through the device when the support structure is expanded. The support structure includes a helical hollow tube that extends around the support structure. Lateral holes extend through the wall of the tube. A therapeutic substance can be infused into the treatment site by supplying the drug into a port at the proximal end of the device. The substance flows through a fluid delivery lumen to the hollow tube along the distal portion of the device. The therapeutic substance flows out of the lateral holes to directly treat the treatment site. The inventions herein may also include any other aspect described below in the written description, the claims, or in the attached drawings and any combination thereof.

BRIEF DESCRIPTION OF SEVERAL VIEWS OF THE DRAWINGS

The invention may be more fully understood by reading the following description in conjunction with the drawings, in which:

FIG. 4 is a side view of the device within a vein; and

FIG. 5 is a side view of the vein with a portion of the thrombus dissolved.

DETAILED DESCRIPTION

Figure 1:
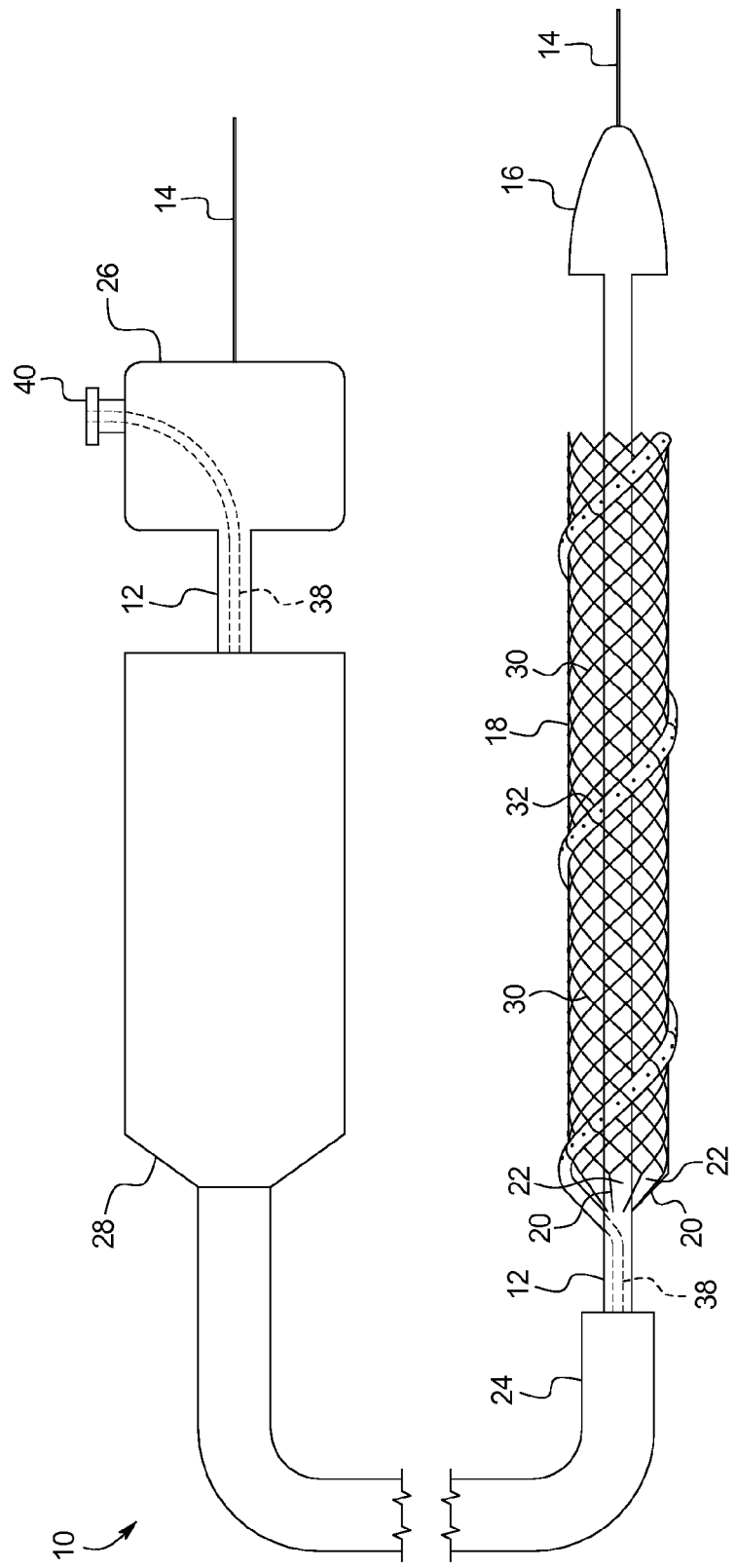
FIG. 1 is a side view of a drug delivery device.
Figure 2:
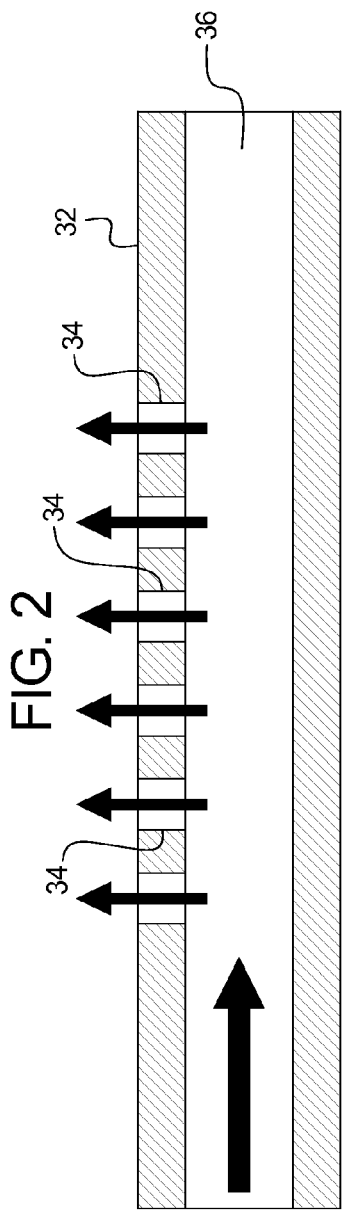
FIG. 2 is a cross-sectional view of a portion of a hollow tube.
Figure 3:
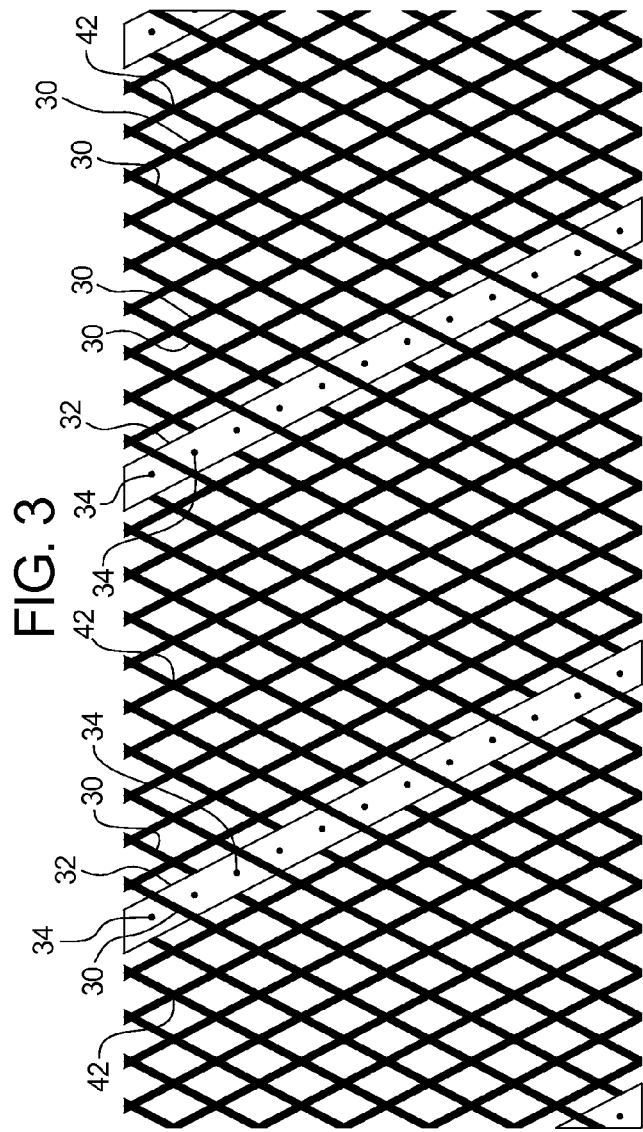
FIG. 3 is an enlarged view of a portion of the support structure.

Referring now to the figures, and particularly to FIGS. 1-3, a drug delivery device 10 is shown, which may be useful for delivering a therapeutic substance directly to a treatment site. As shown in FIG. 1, the device 10 has a proximal portion that remains outside the patient's body during use of the device 10 and a distal portion that passes through an access site into the patient's body. A shaft 12 extends from the proximal portion to the distal portion and allows the device 10 to be maneuvered to the treatment site and removed from the patient's body when the treatment is complete. A guidewire lumen is preferably provided through the shaft 12 for a guidewire 14 to assist in moving the device 10 through the patient's body. The distal end of the shaft 12 may also be provided with an atraumatic tip 16 when the shaft 12 forms the leading edge of the device 10.

A cylindrical support structure 18 is attached to the distal portion of the shaft 12 in a manner that prevents the support structure 18 from being released from the shaft 12. Thus, although the support structure 18 may have a structure that is similar to a stent or other like device, the drug delivery device 10 described herein is not a stent since it does not remain within the patient's body after the treatment is complete. Instead, when the treatment is complete, the support structure 18 is removed from the patient's body with the shaft 12 and any other accessory devices.

The support structure 18 may be attached to the shaft 12 in a variety of ways, but it is critical that blood perfusion (or other bodily fluid) be permitted through the device 10 when the support structure 18 is expanded. For example, the proximal end of the support structure 18 may be attached to the shaft 12 with wires 20, or other connectors 20, that extend from the support structure 18 to the shaft 12. The connectors 20 are preferably flexible to allow the support structure 18 to expand from a compressed configuration to an expanded configuration. The compressed configuration is used during delivery and removal of the device 10 to allow the support structure 18 to assume a low profile (i.e., small diameter) to allow the support structure 18 to travel through a patient's vessel. While the support structure 18 is at the treatment site, the support structure 18 is expanded so that the support structure 18 contacts the wall of the vessel. Thus, in the compressed configuration the support structure 18 will be compressed closer to the diameter of the shaft 12, and in the expanded configuration the support structure 18 will be expanded radially away from the shaft 12.

The wires 20 are preferably equally spaced around the circumference of the shaft 12 and the support structure 18 but do not completely fill the circumferential area between the shaft 12 and the support structure 18. That is, openings 22 are spaced between the wires 20 and between the shaft 12 and the support structure 18 to allow blood to flow through the openings 22 and past the support structure 18 when the support structure 18 is expanded. Although the distal end of the support structure 18 may also be attached to the shaft 12, it may be preferable for the distal end of the support structure 18 to be unconnected to the shaft 12 as shown in FIG. 1. This may provide less obstruction to fluid flow through the device 10 so that the only obstructions include the wires 20 at the proximal end and the shaft 12 itself.

The support structure 18 is preferably self-expanding so that the support structure 18 is biased toward the expanded configuration. The support structure 18 may be retained in the compressed configuration with a restraining sheath 24 that slides over the support structure 18 to prevent the support structure 18 from expanding. Once the support structure 18 is positioned at the intended treatment site, the restraining sheath 24 is withdrawn from the support structure 18. This may be done by providing first and second handle members 26, 28 along the proximal portion of the device 10, where the first handle member 26 is attached to the shaft 12 and the second handle member 28 is attached to the restraining sheath 24. Thus, the first handle member 26 may be longitudinally restrained while the second handle member 28 is pulled in a proximal direction to withdraw the restraining sheath 24. Upon withdrawal of the restraining sheath 24 from the support structure 18, the support structure 18 self-expands outward until the support structure 18 comes into contact with the vessel wall. After the treatment is complete, the support structure 18 may be recompressed to remove the support structure 18 by pushing the second handle member 28 in the distal direction while longitudinally restraining the first handle member 26. This pushes the restraining sheath 24 back over the support structure 18 and forces the support structure 18 to compress and slide back into the restraining sheath 24. The wires 20 may be helpful in recompressing the support structure 18 by providing a transitional structure that guides the restraining sheath 24 over the support structure 18. That is, when the distal end of the restraining sheath 24 moves distally and contacts the wires 20, the force exerted on the wires 20 by the distal end of the restraining sheath 24 may cause the wires 20 to rotate inward toward the shaft 12 and pull the proximal end of the support structure 18 inward toward the collapsed configuration. As the distal end of the restraining sheath 24 continues to be pushed distally, the support structure 18 is squeezed inward by the distal end of the restraining sheath 24 until the restraining sheath 24 covers the entire length of the support structure 18 again. In order to facilitate recompressing the support structure 18 within the restraining sheath 24, the support structure 18 and the wires 20 preferably do not have any unsupported portions that extend in the proximal direction that could be caught on the distal end of the restraining sheath 24 as it is moved distally over the support structure 18. That is, it is preferable for the wires 20 and support structure 18 to be formed from a series of filaments 30 that extend distally without having any bends or ends that face in the proximal direction.

While the preferred support structure 18 is self-expanding as described, it is understood that the support structure 18 may also be mechanically expanded in other ways if desired. For example, as illustrated in FIGS. 4 and 5, the proximal end of the support structure 18 and the distal end of the support structure 18 may be attached to the shaft 12 with various types of connectors 20. In order to mechanically expand the support structure 18, the shaft 12 and connectors 20 may be designed to allow the proximal and distal connectors 20 to move toward each other to expand the support structure 18 and move away from each other to compress the support structure 18. For example, the shaft 12 may be a two piece shaft where a first shaft member is connected to the proximal end of the support structure 18, and a second shaft member is connected to the distal end of the support structure 18. The two members may then be moved relative to each other to expand and compress the support structure 18.

As shown in FIGS. 1 and 3, the support structure 18 includes at least one hollow tube 32 that extends helically around the support structure 18. As shown FIG. 2, the tube 32 has a series of lateral holes 34 that extend radially through the wall of the tube 32 so that a fluid passing through the lumen 36 of the tube 32 can pass out of the tube 32. Preferably, the holes 34 only extend radially outward from the tube 32 so that a drug passing out of the holes 34 is directed outward directly into the wall of the treatment site. Thus, it is preferred that the drug is not directed inward into the lumen of the vessel where it would mix with blood flowing therethrough and therefore more easily flow away. The tube 32 is preferably connected to the support structure 18 and expands and compresses therewith. Although the figures show a single tube 32 in the support structure 18 extending in only one helical direction, it is also possible for the support structure 18 to have more than one tube 32 extending in one helical direction. The support structure 18 may also have tubes 32 extending in both helical directions instead of only one helical direction if desired.

A fluid delivery lumen 38 is also provided along the length of the device 10 to provide a drug supply from outside the patient's body to the lumen 36 and lateral holes 34 of the tube 32 during treatment. For example, the fluid delivery lumen 38 may be a portion of the hollow tube 32 that extends between the support structure 18 and the shaft 12 and may therefore be treated as one of the wires 20. The fluid delivery lumen 38 may then extend through the shaft 12 to the first handle member 26 where a port 40, such as a luer fitting 40, may be provided for connecting a drug supply to the fluid delivery lumen 38. The drug supply may be provided in various ways, such as by using a syringe connected to the drug supply port 40. As described, the drug then passes through the fluid delivery lumen 38 in the shaft 12 to the portion of the tube 32 that connects the shaft 12 to the support structure 18. From the inside of the helical tube 32, drug passes from the tube lumen 36 out of the lateral holes 36 to the treatment site. The distal end of the tube 32 may be plugged if desired to prevent the drug from escaping through the distal end.

As shown in FIG. 3, the support structure 18 may be formed as a braided structure of filaments 30, where the filaments 30 pass over and under each other at the junctions 42. Thus, a portion of the filaments 30 extend spirally around the wall of the support structure 18 in a first direction, and another portion of the filaments 30 extend spirally around the wall of the support structure 18 in a second direction. Thus, the filaments 30 spiral around the structural wall in opposite directions, in the sense that the first portion of filaments 30 may extend around in a clockwise direction and the second portion of filaments 30 may extend around in a clockwise direction. Where the filaments 30 cross 42 each other, the two filaments 30 pass over and under each other. For example, when a first element 30 crosses a second filament 30, the first filament 30 may pass over the second filament 30. When the first element 30 crosses the next filament 30, the first filament 30 will pass under the next filament 30. Thus, the wall of the support structure 18 is formed of a braided structure with the filaments 30 alternatively passing over and under each other. If desired, the connecting wires 20 may be extensions of the braided filaments 30 that make up the support structure 18. Alternatively, where the braided support structure 18 is made of a single wire that is wound back-and-forth between the ends of the support structure 18, the connecting wires 20 may be separate wires 20 that are attached to the support structure 18 by welding or other attachment methods.

Although the hollow tube 32 may be connected to the support structure 18 in various ways, the tube 32 may be interlaced with the wall of the support structure 18. For example, where the support structure 18 is a braided structure, the tube 32 may be braided into the support structure 18 as one or more of the filaments 30 of the braid as shown in FIG. 3. Because the tube 32 is required to have a lumen 36 extending therethrough for the passage of fluids, it may be desirable for the tube 32 to have a larger outer diameter than the remaining filaments 30 of the support structure 18. It is also possible for the tube 32 to be stiffer than the other filaments 30 in the support structure 18 so that the tube 32 exerts more individual outward radial force than the other filaments 30. This may be desirable so that the outwardly facing holes 34 in the tube 32 are pressed solidly against the vessel wall to ensure that the drug is infused directly into the vessel wall. Although various materials may be used for the tube 32 and the support structure 18, it may be desirable for the tube 32 and the other filaments 30 to both be made from metal, such as nitinol or stainless steel. The tube 32 may also be made from metal while the remaining filaments 30 of the support structure 18 are made from a non-metal mesh.

As shown in FIGS. 4-5, the device 10 may be useful for treating a thrombus 44 within a vein 46. Thus, as shown in FIG. 4, the support structure 18 may be expanded within the vein 46 at the site of the thrombus 44 as described above. As a result, the thrombus 44 will be squeezed between the outer surface of the support structure 18 and the wall 48 of the vein 46. An anti-thrombotic drug, such as tPA or heparin, may then be infused through the hollow tube 32 so that the drug exits the lateral holes 34 outwardly into the thrombus 44. Because the drug is not merely infused into the lumen of the vein 46, it is possible that less drug may be needed to treat the thrombus 44 since the drug may be directed straight into the thrombus 44. As shown in FIG. 5, the thrombus 44 may dissolve at a greater rate directly around the tube 32 so that portions 50 of the thrombus 44 extend inward between adjacent windings of the tube 32.

One advantage of the device 10 is that the device 10 may be maintained in the expanded configuration at the treatment site longer than other drug delivery devices. In other words, because blood 52 is able to continue flowing through the vein 46 while the support structure 18 is expanded and the drug is being infused through the holes 34, the device 10 can stay in place and the drug treatment can be continued without worrying about starving downstream tissues of blood flow 52. Thus, in contrast to devices that rely on balloons for drug delivery which must be removed after only minutes of treatment, drug treatments with the described device 10 can be maintained for five minutes or more. Thus, more complete treatment of a thrombus 44 or other condition may be possible.

In FIG. 5, it may be sufficient to continue the drug treatment for a prolonged period of time to reach the desired level of thrombus 44 dissolution before removing the support structure 18 from the vein 46 by pulling proximally on the shaft 12. Alternatively, the support structure 18 may be withdrawn proximally while the support structure 18 remains expanded. Thus, where portions 50 of the thrombus 44 extend inward between windings of the tube 32 like in FIG. 5, the tube 32 will slide along the vessel wall 48 and break the extending portions 50 away from the thrombus 44. The loosened thrombotic material may be aspirated out of the vein 46 either with the restraining sheath 24 or another aspirating catheter, or a trap or basket may be released before the procedure to catch loosened material.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

The invention claimed is:

1. An intraluminal drug delivery device, comprising:
a shaft adapted to extend from a proximal portion outside an access site into a patient's body to a distal portion within said patient's body;
a cylindrical support structure disposed along said distal portion of said shaft, said support structure being expandable between a compressed configuration and an expanded configuration;
a plurality of connectors attaching a proximal end of said support structure to said shaft, said connectors allowing said support structure to expand away from said shaft, wherein a plurality of openings are disposed between said connectors and between said shaft and said support structure, a bodily fluid thereby being permitted to flow through said openings and past said support structure when said support structure is expanded and wherein a distal end of said support structure is unconnected to said shaft;
at least one hollow tube extending helically around said support structure and being compressible and expandable therewith, said at least one hollow tube comprising a plurality of lateral holes extending through a wall of said at least one hollow tube to provide fluid communication between a lumen extending therethrough and an exterior of said at least one hollow tube; and
a fluid delivery lumen in communication with said lumen of said at least one hollow tube, said fluid delivery lumen extending from said hollow tube to a proximal end adapted to be disposed outside said access site, a therapeutic fluid thereby being deliverable through said fluid delivery lumen and said lumen of said at least one hollow tube and exiting through said holes, wherein said holes extend from said lumen of said at least one hollow tube radially outward.

2. The intraluminal drug delivery device according to claim 1, wherein said holes do not extend radially inward.

3. The intraluminal drug delivery device according to claim 1, wherein said support structure is self-expanding, and further comprising a restraining sheath disposed around said support structure and said at least one hollow tube to retain said support structure and said at least one hollow tube in said compressed configuration, said support structure and said at least one hollow tube expanding to said expanded configuration upon withdrawing said restraining sheath from said support structure and said at least one hollow tube.

4. The intraluminal drug delivery device according to claim 1, wherein said at least one hollow tube is interlaced with a wall of said support structure.

5. The intraluminal drug delivery device according to claim 1, wherein said support structure comprises filaments having an outer diameter and forming a braided structure of filaments, said at least one hollow tube being braided with said filaments.

6. The intraluminal drug delivery device according to claim 5, wherein said at least one hollow tube comprises a larger outer diameter than said outer diameter of said filaments forming said braided structure of said filaments.

7. The intraluminal drug delivery device according to claim 1, wherein said at least one hollow tube is stiffer than filaments comprising said support structure.

8. The intraluminal drug delivery device according to claim 1, wherein said at least one hollow tube and filaments comprising said support structure are made of metal.

9. The intraluminal drug delivery device according to claim 1, wherein said at least one hollow tube is a plurality of said hollow tubes, wherein said plurality of said hollow tubes extend around said support structure in only one direction, none of said plurality of said hollow tubes thereby extending around said support structure in an opposite direction.

10. The intraluminal drug delivery device according to claim 1, wherein said at least one hollow tube is a single tube.

11. The intraluminal drug delivery device according to claim 1, wherein said fluid delivery lumen extends through said shaft.

12. The intraluminal drug delivery device according to claim 1, wherein said holes do not extend radially inward, and said at least one hollow tube is interlaced with a wall of said support structure.

13. The intraluminal drug delivery device according to claim 12, wherein said support structure is self-expanding, and further comprising a restraining sheath disposed around said support structure and said at least one hollow tube to retain said support structure and said at least one hollow tube in said compressed configuration, said support structure and said at least one hollow tube expanding to said expanded configuration upon withdrawing said restraining sheath from said support structure and said at least one hollow tube, and said support structure comprises filaments having an outer diameter and forming a braided structure of said filaments, said at least one hollow tube braided with said filaments.

14. The intraluminal drug delivery device according to claim 13, wherein said at least one hollow tube comprises a larger outer diameter than said outer diameter of said filaments, and wherein said at least one hollow tube extends around said support structure in only one direction.

15. The intraluminal drug delivery device according to claim 14, wherein said at least one hollow tube is stiffer than said filaments, said at least one hollow tube and said filaments are made of metal, and said fluid delivery lumen extends through said shaft.

16. The intraluminal drug delivery device according to claim 1, wherein the at least one hollow tube is a plurality of said tubes wherein said holes do not extend radially inward, and said plurality of said tubes extend around said support structure in only one direction, none of said plurality of said tubes thereby extending around said support structure in an opposite direction.

17. The intraluminal drug delivery device according to claim 16, wherein said plurality of said tubes are interlaced with a wall of said support structure.

18. The intraluminal drug delivery device according to claim 1, wherein said support structure comprises a braided structure of filaments, said at least one hollow tube being braided with said filaments and wherein said at least one hollow tube is a single tube.

* * * * *